US009671324B2

(12) United States Patent
Drinovec et al.

(10) Patent No.: US 9,671,324 B2
(45) Date of Patent: Jun. 6, 2017

(54) METHOD AND APPARATUS TO COMPENSATE ANALYTICAL DEVICES THAT COLLECT CONSTITUENTS OF INTEREST ON A FILTER FOR THE EFFECT OF FILTER LOADING

(71) Applicant: Aerosol d.o.o., Ljubljana (SI)

(72) Inventors: Luka Drinovec, Ljubljana (SI); Grisa Mocnik, Ljubljana (SI); Anthony D. A. Hansen, Berkeley, CA (US)

(73) Assignee: AEROSOL D.O.O., Ljubljana (SI)

( * ) Notice: Subject to any disclaimer, the term of this patent is extended or adjusted under 35 U.S.C. 154(b) by 0 days.

(21) Appl. No.: 14/695,764

(22) Filed: Apr. 24, 2015

(65) Prior Publication Data

US 2016/0313229 A1    Oct. 27, 2016

Related U.S. Application Data

(60) Provisional application No. 61/983,663, filed on Apr. 24, 2014.

(51) Int. Cl.
*G01N 15/06* (2006.01)
*G01N 15/10* (2006.01)
*G01N 21/31* (2006.01)
*G01N 21/59* (2006.01)

(52) U.S. Cl.
CPC ..... *G01N 15/0625* (2013.01); *G01N 15/1012* (2013.01); *G01N 21/31* (2013.01); *G01N 21/59* (2013.01); *G01N 2201/127* (2013.01)

(58) Field of Classification Search
CPC ... G01N 2201/127; G01N 2201/12746; G01N 15/0625; G01N 21/31; G01N 15/0631; G01N 15/0618; G01N 21/59; G01N 15/1012; G01N 21/274
See application file for complete search history.

(56) References Cited

U.S. PATENT DOCUMENTS

| | | |
|---|---|---|
| 3,204,449 A | 9/1965 | Fordyce |
| 3,419,879 A | 12/1968 | Pelavin |
| 3,489,525 A | 1/1970 | Natelson |
| 3,526,480 A | 9/1970 | Findl et al. |

(Continued)

FOREIGN PATENT DOCUMENTS

| | | |
|---|---|---|
| EP | 2 151 679 A2 | 2/2010 |
| JP | 2001343319 A | 12/2001 |

OTHER PUBLICATIONS

Aerosol d.o.o., European Patent Application No. 15165111.4—Extended Search Report, Sep. 15, 2015.

(Continued)

*Primary Examiner* — Michael P LaPage
(74) *Attorney, Agent, or Firm* — Steven R. Vosen

(57) ABSTRACT

An apparatus and method are presented for the analysis of materials. The apparatus includes two or more similar analyzers, with the output of the analyzers combined to provide improved measurements. The apparatus may be, for example, a differential photometric analyzer, such as the AETHALOMETER®. The apparatus includes a processor programmed to accept an instrument constant determined at low filter loadings and use the constant to compensate for non-linear instrument responses. A method is also presented for conditioning filters before use.

14 Claims, 2 Drawing Sheets

(56) References Cited

U.S. PATENT DOCUMENTS

| | | | |
|---|---|---|---|
| 3,653,773 A | 4/1972 | Childs | |
| 3,654,801 A | 4/1972 | Keefer et al. | |
| 3,690,833 A | 9/1972 | Ferrari Andres | |
| 3,769,505 A | 10/1973 | Lee et al. | |
| 3,770,356 A | 11/1973 | Kimura | |
| 3,837,808 A | 9/1974 | Sugimoto et al. | |
| 3,975,727 A | 8/1976 | Mader et al. | |
| 4,123,159 A | 10/1978 | Hollander et al. | |
| 4,395,493 A | 7/1983 | Zahniser et al. | |
| 4,543,815 A | 10/1985 | Troup et al. | |
| H572 H | 2/1989 | Hansen | |
| 4,893,934 A | 1/1990 | Hansen | |
| 4,942,297 A * | 7/1990 | Johnson | G01N 15/02 250/304 |
| 6,406,633 B1 | 6/2002 | Fischer et al. | |
| 7,038,765 B2 | 5/2006 | Petzold et al. | |
| 7,168,292 B2 | 1/2007 | Gundel et al. | |
| 8,299,449 B2 | 10/2012 | Febo | |
| 8,411,272 B2 | 4/2013 | Hansen | |
| 2004/0156036 A1 | 8/2004 | Petzold et al. | |
| 2005/0041774 A1 | 2/2005 | Saitoh et al. | |
| 2008/0100826 A1 | 5/2008 | Sharpe | |
| 2009/0081804 A1 | 3/2009 | Tuchman | |
| 2010/0027013 A1 * | 2/2010 | Hansen | G01N 21/4738 356/432 |
| 2010/0265508 A1 | 10/2010 | Schumann et al. | |
| 2012/0229798 A1 * | 9/2012 | Mocnik | G01N 15/0618 356/51 |

OTHER PUBLICATIONS

L.A. Gundel et al., "The relationship between optical attenuation and black carbon concentration for ambient and source particles", The Science of the Total Environment, vol. 36, Jul. 1, 1984, pp. 197-202, XP055211688, DOI: doi.10.1016/0048-9697 (84) 90266-3.

Batelle; Environmental Technology Verification Report, "Magee Scientific Aethalometer Particulate Carbon Monitor"; Aug. 2001.

Petzold, Andreas et al., 'Method Comparison Study on Soot-Selective Techniques,' 1995, Mikrochimica Acta 117, pp. 215-237.

Hanel, Gottfried, 'Radiation Budget of the Boundary Layer. Part II: Simultaneous Measurement of Mean Solar Volume Absorption and Extinction Coefficients of Particles,' 1987, Beitr. Phys. Atmosph. vol. 60, No. 2.

Aerosol d.o.o., European Patent Application No. 09009991.2—Extended Search Report, Jul. 16, 2013.

* cited by examiner

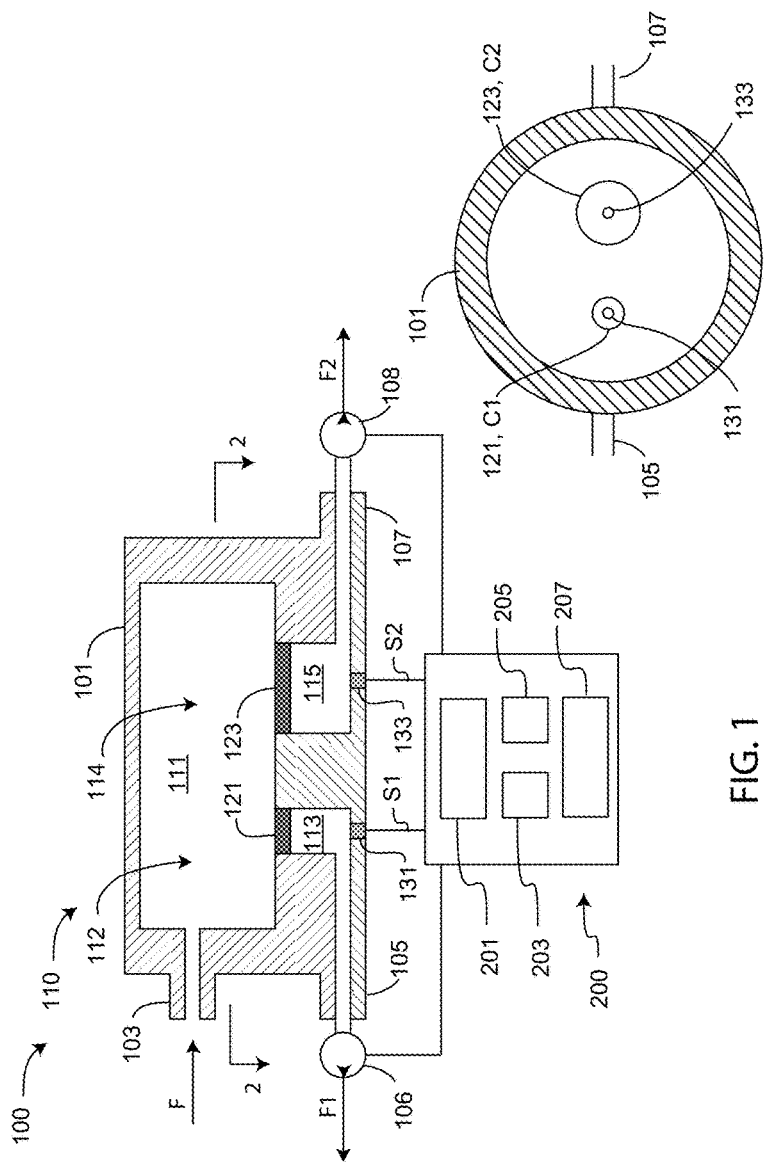

METHOD AND APPARATUS TO COMPENSATE ANALYTICAL DEVICES THAT COLLECT CONSTITUENTS OF INTEREST ON A FILTER FOR THE EFFECT OF FILTER LOADING

CROSS-REFERENCE TO RELATED APPLICATIONS

This application claims the benefit of U.S. Provisional Application No. 61/983,663, filed Apr. 24, 2014, the entire contents of which are incorporated herein by reference and made part of this specification.

TECHNICAL FIELD

Aspects relate, in general, to a method and apparatus for measuring constituents of interest in a sample analysis, and more specifically to a method and apparatus to improve the analysis of chemical, physical or biological materials.

BACKGROUND

Most instruments for characterizing a material of interest rely on indirect measurements of a property of interest. Typically, there is an assumed functional relationship between a measured quantity and a property of interest. Thus, for example, there is a linear relationship between the mass and the weight of an object. Accordingly, a simple calibration of a scale allows the mass of an object to be inferred from a measure of the object's weight.

Some instruments have more complex responses. Thus, for example, the electric potential of a thermocouple is a non-linear function of the thermocouple temperature. Since thermocouples are well characterized, a polynomial function may be used to convert the thermocouple output into a temperature. Thus measurements performed by techniques that are well-understood or well-characterized, may be used to a high degree of accuracy.

However, some instruments may have responses that are not understood well enough to generally compensate for biases in the instrument response. Thus, for example, if certain effects alter the output of an instrument and are not taken into account, then the use of the instrument may produce inaccurate measurements.

There exists a need for methods and systems to provide for improved accuracy of measurements having complex responses. Such methods and systems should provide improved accuracy by not utilizing derivatives of measured values.

SUMMARY

The present invention is an apparatus and method that compensates for certain instrument biases in the measurements of analytical instruments.

Certain embodiments provide an apparatus to measure constituents of interest in a sample having a concentration, B. The apparatus includes a first analyzer, a second analyzer, and a processing device. The first analyzer includes a first filter portion having a first area, $C1$, to accumulate constituents of interest in a first portion of the sample having a first flow rate, $F1$, and a detector to measure a first attenuation as a function of time, $A1$, of the constituent of interest on said first filter and provide a measure of $B=B1$. The second analyzer includes a second filter portion having a second area, $C2$, to accumulate constituents of interest in a second portion of the sample having a second flow rate, $F2$, and a detector measure a second attenuation as a function of time, $A2$, of the constituent of interest on the second filter and provide a measure of $B=B2$. The processing device has a processor programmed to accept the first detector and second detector measurements and provide an indication of the constituents of interest in the flow. The processor is programmed to determine an estimate the concentration of the constituents of interest in the execute the steps of: accepting an instrument calibration, $P$, where $P$ is determined for the instrument in the limit of $A1 \rightarrow 0$, determining current values of $F1$ and $F2$, determining current values of $A1$ and $A2$, and solving for the concentration $B$ of the constituents of interest in the sample using a model including $C$, $F1$, $A1$, $B1$, $F2$, $A2$, $B2$, and $B$.

Certain other embodiments provide a method for measuring constituents of interest in a sample having a concentration, $B$, performed in an apparatus including a first analyzer including a first filter portion having a first area, $C1$, and a first detector; and a second analyzer including a second filter portion having a second area, $C2$, and a second detector. The method includes: accumulating constituents of interest in a first portion of the sample having a first flow rate, $F1$, at the first analyzer; measuring a first attenuation of the constituent of interest on said first filter as a function of time, $A1$; determining a first measure of $B$, $B1$; accumulating constituents of interest in a second portion of the sample having a second flow rate, $F2$, at the second analyzer; measuring a second attenuation of the constituent of interest on the second filter as a function of time, $A2$; determining a second measure of $B$, $B2$; and determining an estimate of the concentration of the constituents of interest by receiving an instrument calibration, $P$, where $P$ is determined for the apparatus in the limit of $A1 \rightarrow 0$, determining current values of $F1$ and $F2$, determining current values of $A1$ and $A2$, and calculating for the concentration $B$ of the constituents of interest in the sample using $C$, $F1$, $A1$, $B1$, $F2$, $A2$, $B2$, and $B$.

Certain embodiments provide a computer program product, comprising a computer usable medium having computer readable program code embodied therein, said computer readable program code adapted to be executed to implement a method for measuring constituents of interest in a sample.

Certain other embodiments provide a method of operating an apparatus including at least one filter to collect constituents of interest in a sample and an analyzer to determine a concentration of the constituent of interest from measurements on each of the at last one filter. The method includes: removing at least a portion of the constituents of interest from the sample; providing the sample from which at least a portion of the constituents of interest is removed to the filter for a conditioning time; providing the sample to the filter after the conditioning time; and analyzing the filter to determine an amount of the constituents of interest.

In certain embodiments, an apparatus includes a differential photometric analyzer. In certain other embodiments the differential photometric analyzers are included in an instrument that uses optical analysis to determine the mass concentration of Black Carbon particles collected from an air stream passing through a filter.

BRIEF DESCRIPTION OF THE DRAWINGS

Certain features together with various ancillary provisions and features which will become apparent to those skilled in the art from the following detailed description, are attained by the apparatus and method of the present invention, preferred embodiments thereof being shown with reference to the accompanying drawings, by way of example only, wherein:

FIG. 1 a schematic of a first embodiment of a system;
FIG. 2 is a sectional view 2-2 of FIG. 1.

Figures 3, 4:
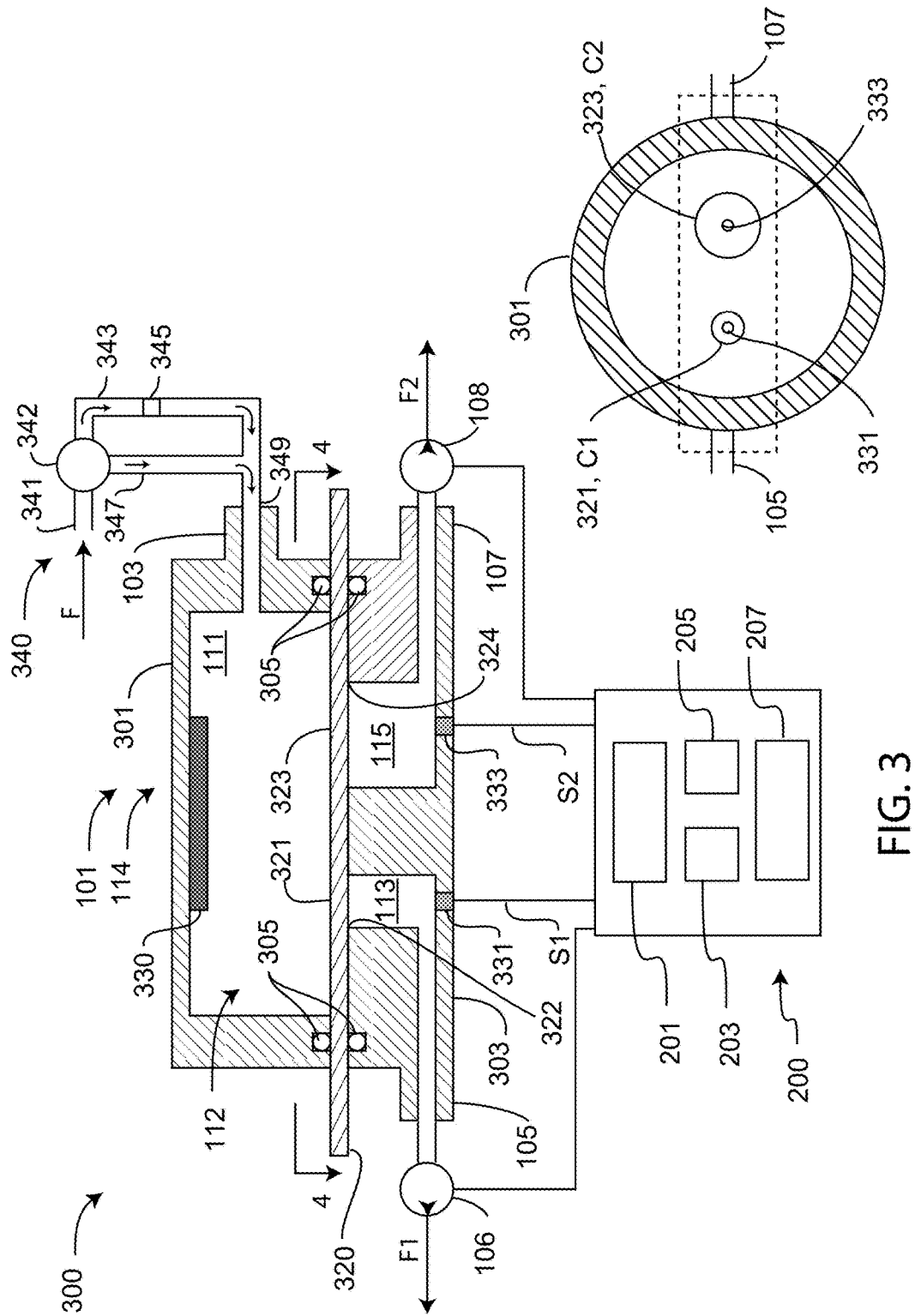
FIG. 3 a schematic of a second embodiment a system.
FIG. 4 is a sectional view 4-4 of FIG. 3.

Reference symbols are used in the Figures to indicate certain components, aspects or features shown therein, with reference symbols common to more than one Figure indicating like components, aspects or features shown therein.

DETAILED DESCRIPTION

Example embodiments are described below in sufficient detail to enable those of ordinary skill in the art to embody and implement the systems and processes herein described. It is important to understand that embodiments can be provided in many alternate forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

The terminology used herein to describe embodiments is not intended to limit the scope. The articles "a," "an," and "the" are singular in that they have a single referent, however the use of the singular form in the present document should not preclude the presence of more than one referent. In other words, elements referred to in the singular can number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Unless otherwise defined, all terms (including technical and scientific terms) used herein are to be interpreted as is customary in the art. It will be further understood that terms in common usage should also be interpreted as is customary in the relevant art and not in an idealized or overly formal sense unless expressly so defined herein.

Various embodiments described herein are directed to analytic devices, systems, and methods that permit the identification, characterization, or quantification of one or more constituents of interest, such as an analyte, a biological component, or particulates. In particular, devices, systems, and methods are discussed that advantageously combine the output from multiple measurements of a sample, such as a flow of a gas containing a constituent of interest.

FIG. 1 is a schematic of the cross-section of one embodiment of a system 100 and FIG. 2 is a sectional view 2-2 of the embodiment of FIG. 1. System 100 includes an instrument 110 which may be in communication with a processing device 200.

In general, instrument 110 is configured to accept a sample and perform measurements on two or more portions of the sample. By way of an example, which is not meant to limit the scope of the invention, FIG. 1 shows a flow F of a sample which is divided into two flows, F1 and F2, which are then analyzed separately. Instrument 110 thus may include one or more analyzers, each configured to measure a constituent of interest in each portion of the sample. In one embodiment, each measurement is essentially the same type of analysis, and the results of the separate analysis are combined and/or analyzed in the processing device 200 to provide a more accurate indication of the constituent of interest. As described subsequently, measurements from different portions of a sample may be used, for example and without limitation, to obtain the improved accuracy over any one of the measurements, or to determine sample-dependent biases of an individual instrument calibration.

In one embodiment, instrument 110 may include a housing 101 having an inlet 103, a first outlet 105 having an associated first pump 106 and a second outlet 107 having an associated second pump 108. Housing 101 defines an interior that includes a volume 111 in fluid communication with inlet 103, a volume 113 in fluid communication with first outlet 105, and a volume 115 in fluid communication with outlet 107.

In one embodiment, first pump 106 may operatively draw flow from the apparatus through first outlet 105 at a flow rate F1, and a second pump 108 may operatively draw flow from the apparatus through second outlet 107 at a flow rate F2. Fluid thus enters inlet 103 with a flow rate F=F1+F2, and is divided into two streams within instrument 110. Alternatively, a single pump may be connected to both outlets 105 and 107, and valves, orifices or other means may be provided to alter flow rates F1 and F2. System 100 may also include flow meters and/or flow controllers to measure or control one or more of flows F, F1, or F2. System 100 may thus separate flow F into flows F1 and F2 by providing volumes 111, 113, and 115 for the inlet fluid.

Instrument 110 includes multiple analyzers, shown for example and without limitation in FIG. 1 as a first analyzer 112 and a second analyzer 114. Instrument 110 may thus accept a sample and provide portions to each analyzer, shown for example and without limitation as a portion F1 provided to first analyzer 112, and as second portion provided to second analyzer 114. Analyzers 112 and 114 are configured to perform measurements on the samples within volumes 113 and 115, respectively and produce an output S1 and S2, respectively. Thus, for example, analyzer 112 includes a sensor 131 that performs a measurement on the sample within volume 113 and analyzer 114 includes a sensor 133 that performs a measurement on the sample within volume 115. Sensors 131 and 133 may be, for example, a combination of light source and detector that measure light absorption within volumes 113 and 115, respectively.

In another embodiment, analyzers 112 and 114 each perform a measurement on constituents of interest that is accumulated on a corresponding filter material, which may be a porous material through with the sample passes. Thus, for example, analyzer 113 may include a filter 121 and sensor 131 associated with volume 113, where sensor 131 is adapted to perform a measurement on constituents of interest that have accumulated on filter 131, having a collection area of C1, and analyzer 114 may include a filter 123, having a collection area of C2, and sensor 133 associated with volume 115, where filter 123 is adapted to perform a measurement one constitutions of interest that may have accumulated on filters 123. In one embodiment filters 121 and 123 are positioned and adapted to collect particulates by filtration from sample flows of sample portions F1 and F2 that pass through volumes 113 and 115, respectively. Sensors 131 and 133 may be a combination of light source and detector that measure light absorption within filters 121 and 123. In general, as the amount of constituents of interest accumulate on areas C1 and C2, the output of sensors 131 and 133, that is, S1 and S2 decrease due to interaction of the particulates of interest and light passing through the filters.

In certain embodiment, flow rates F1 and F2 are held constant while areas C1 and C2 accumulate constituents of interest. As a result of the accumulation of constituents of interest on areas C1 and C2, the output of sensors 131 and 133 (S1 and S2, respectively) will decrease due to the interaction of light passing through areas C1 and C2 by the particulates of interest.

A processing device 200 includes a processor 201 and a memory 203. Memory 203 includes programming to control the operation of system 100 and to process the outputs S1 and S2 from sensors 131 and 133, respectively. Memory 203 may also store, for example and without limitation, previous sensor outputs, including but not limited to background readings (without a filter, or with a fresh filter having no deposits), the results of previous measurements, and programming to permit the processing device 200 to execute mathematical algorithms to convert the sensor output into some indication of one or more constituents of interest.

The processing device 200 may also include display 207 to present an indication of a constituent of interest, which may be, for example and without limitation, a concentration of a constituent of interest or a direct or indirect measurement related to the constituent of interest. The processing device 200 may further include communications interface 205 which may be used to transmit an indication of a constituent of interest to another computer or system, either wirelessly or over a wired network. The processing device 200 may also provide signals to control pumps 106 and 108 and/or to accept input from flow controllers that may be associated with the pumps.

In certain embodiments, system 100 is an analytical instrument that performs measurements on particulates deposited on filters 121 and 123. In certain embodiments, sensors 131 and 133 produce readings that are proportional to the amount of particulates deposited on filters 121 and 123, respectively. Thus, for example, sensors 131 or 133 may be calibrated to provide an estimate of the concentration of particulates suspended in the fluid flow F, based on measurements of light absorption through filters 121 and 123. In some instances, the calibration is proportional to the logarithm of light absorption, for example. It is known that for some measurements such as optical transmission through a filter with deposits of optically-absorbing matter, calibrations derived for low amounts of particulate loading may not apply at high amounts of loading, and that the instrument's sensitivity to the particulate concentration changes in a manner that depends on the type of particulates and their density on the filter.

Examples of sensors 131 and 133 include, but are not limited to: optical sensors for the measurement of transmission through and/or reflection from particulate filters. One class of instruments is differential photometric analyzers, wherein the differences between sequential optical measurements are used to determine particulate concentrations, such as the AETHALOMETER® instrument (Magee Scientific Company, Berkeley Calif.) (see for example, U.S. Pat. No. 4,893,934, incorporated herein by reference); or the Multi Angle Absorption Photometer (see, for example, U.S. Pat. No. 7,038,765), or the Particle Soot Absorption Photometer (see, for example, Bond, T. C., Anderson, T. L., Campbell, D., "Calibration and intercomparison of filter-based measurements of visible light absorption by aerosols," Aerosol Science and Technology, vol. 30, pp 582-600, 1999). System 100 may also be, for example and without limitation, an apparatus that detects electrons transmitted through a filter, as in instruments such as the Beta Attenuation Mass Monitor (see, for example, Macias, E. S.; Husar, R. B., "Atmospheric particulate mass measurement with beta attenuation mass monitor," Environmental Science and Technology, vol. 10, September 1976, p. 904-907); measurements of the vibrational frequency of the filter, as in instruments such as the Tapered Element Oscillating Microbalance (see, for example, Patashnick, H.; Rupprecht, G. "The tapered element oscillating microbalance: A monitor for short-term measurement of fine aerosol mass concentration", Final Report, October 1977-December Dudley Observatory, Albany, N.Y., 1980.); changes in the electrical properties in volumes 113 and 115, as in instruments such as electrochemical gas analyzers; measurements of radiation from radioactive particulates; or measurements of magnetic properties in the filter.

In one embodiment, the relationship between a useful measure of the constituent of interest and the outputs S1 and S2 may depend on two parameters, such as a linear term and a non-linear term, or a combination of a linear and non-linear function. Given two measurements and two parameters, processing device 200 may be programmed to accept the sensor outputs S1 and S2, and manipulate these signals to compute, for example, a determination of the concentration of the constituent of interest. Examples of such methods are discussed subsequently. Thus system 100 is thus capable of combining two measurements of portions of a flow to provide greater accuracy of a concentration or some characteristic of a constituent of interest. In one embodiment, system 100 may be configured such that each filter 121 and 123 has a different rates of accumulation of constituents of interest (by having different area or flow rates, for example), and combines the signal outputs of sensors 131 and 133 in a manner to provide an improved accuracy by including higher order terms. Several embodiments that utilize different filter loadings are discussed subsequently.

While the embodiment of FIG. 1 illustrates a system 100 that performs two measurements, it is clear to one skilled in the art that other variations are within the scope of the present invention. Thus, for example and without limitation, system 100 may include: a flow-diversion device that accepts a sample and then provides portions of the sample to two separate instruments, where the portions are provided continuously or sequentially to the instruments; or more than two measurements. Further, the analyzers of instrument 110 may be within a housing 101, as in FIG. 1, or alternatively, the analyzers may be in separate housings, and/or some or all of the processing device 200 or other electronics may reside within housing 101 or separate housings for individual analyzers. In another alternative embodiment, analyzers such as 112 and 114 may share certain components, such as a common light source or a common sensor, that are configured to measure signals derived from different portions of the flow.

FIG. 3 is a schematic of the cross-section of another embodiment of a system 300 and FIG. 4 is a sectional view 4-4 of the embodiment of FIG. 4, and which may be generally similar to system 100, except as further detailed below.

In one embodiment, system 300 has an in-line filter that collects particulates, such as "Black Carbon" (or "BC") particles, and measures light absorption through the filter over time. Sequential measurements may be used to estimate the density of particles in the sample, as discussed subsequently. System 300 includes a fibrous filter tape 320 which may be, for example and without limitation, a filter tape of fibrous material that is intended for performing optical transmission measurements for the determination of the presence of particulates. Housing 101 includes a top cover, or inlet housing 301 and an outlet housing 303 and seals 305 through which tape 320 passes through the housing. For example and without limitation, seals 305, which may be O-rings, may permit fresh filters to be provided to system 300 without opening the apparatus, with a minimum of interruption, and without the exchange of gases between the environment and the apparatus, except through inlet 103 and outlets 105 and 107.

Outlet housing 303 has an opening 322 that forms one side of volume 113 with an area C1 and an opening 324 that forms one side of volume 115 with an area C2. Tape 320 is positioned over openings 322 and 324 so that a portion of the tape is a filter 321 which covers opening 322, and which has a collection area of C1, and a portion of the tape is a filter 323 which covers opening 324, and which has a collection area of C2.

As particulates accumulate on filters 321 and 323, the attenuation of light through the filter increases to the point where the accuracy of the measurements is degraded. Tape 320 may therefore be replaced or advanced to provide fresh surfaces of filters 321 and 323. This action of changing the tape is called a "tape advance". In one embodiment, a mechanism (not shown) may pull the tape forwards to provide fresh filters 321 and 323. In another embodiment, tape 320 is a single-use cartridge that may be replaced manually or by a mechanism (not shown).

In one embodiment, pumps 106 and 108 reduce the pressure at outlets 105 and 107, drawing flow F from the environment and dividing the flow into flow rates F1 and F2 through the areas of filters 321 and 323, respectively and which are held against output housing 303.

In another embodiment, an inlet control system 340 may be used to pre-filter the sample before being analyzed. Specifically, system 340 controls the flow F into inlet 103, and includes, for example and without limitation, an inlet 341 for accepting a flow F to be sampled, a valve 342, a first line 343 having an in-line filter 345, a second line 347, and an outlet 349 that is connected to inlet 103. Valve 342, which is controlled by processing device 200, diverts flow from inlet 341 through either first line 343 or second line 347 before entering inlet 103. In a first setting, valve 342 diverts flow F from inlet 341, through first line 343, where it passes through filter 345, and into inlet 103. Filter 345, which may be generally similar to the filter 320, removes the particulates of interest in flow F before they are analyzed by system 300. In a second setting, valve 342 diverts flow F from inlet 341, through second line 347 and into inlet 103. Inlet control system 340 thus, by the action of valve 342, may provide flow that is either: 1) consisting of the carrier fluid stream, but from which constituents of interest have been filtered out, or 2) which contains the sample to be analyzed, including the constituents of interest.

System 300 also includes a light source 330 and photo-detectors 331 and 333. Light source 330 is positioned to illuminate both of filters 321 and 323, and photo-detectors 331 and 333 are configured to detect the transmission of light from the light source through filters 321 and 323, respectively. Photo-detectors 331 and 333 provide outputs S1 and S2, respectively, to the processing device 200.

In the embodiment of FIG. 3, analyzer 112 includes light source 300, filter 321 and photo-detector 331, and analyzer 114 includes the shared light source, filter 323 and photo-detector 333.

In one embodiment, photo-detectors 331 and 333 each produce a single output. Thus, for example, broadband transmission may be detected with a broadband light source 330 and photo-detectors 331 and 333. Alternatively, a monochromatic light source 330, or the placement of an optical filter over a broadband light source, allows photo-detectors 331 and 333 to measure transmission at one wavelength or a wavelength band. In another embodiment, measurements are obtained at more than one wavelength, denoted as "N" wavelengths, where (in some instruments) N may equal 2, 3, 7, or another number. Thus, for example, light source 300 may include several emitters, each at a different wavelength. By cycling through the emitters, photo-detectors 331 and 333 may measure the transmission of light at the several wavelengths, resulting in a plurality of signals, denoted as $S1(i)$ and $S2(i)$ where the index I ranges from 1 to N. The use of a plurality of absorptions measurements in a differential photometric analyzer is described, for example, in Fialho et al., "The Aethalometer calibration and determination of iron concentration in dust aerosols," Journal of Aerosol Science, Volume 37, pages 1497-1506, (2006); or Favez et al. "Ambient measurements of light-absorption by agricultural waste burning organic aerosols," Journal of Aerosol Science, Volume 40, pages 613-620, (2009).

The operation of a single wavelength system 300 will now be discussed. It will be appreciated by those skilled in the art that the discussion also is applicable to system 100.

System 300 may be used to measure particulates, such as soot, in the air. With filters 321 and 323 in place and light source 330 turned on, a background reading $S1(0)$ and $S2(0)$ is taken of photo-detectors 331 and 333, respectively in the absence of particulates on the filter.

Next, pumps 106 and 108 are started, and air at a flow rate F is drawn into inlet 103. The air settles in volume 111 and is drawn into one of the two sampling portions of system 300. Specifically, flow rate F1 is drawn through the area C1 of filter 321 and flow rate F2 is drawn through area C2 of filter 323. Tape 130 may be advanced before the filters become saturated with particulates.

In an alternative embodiment, the order of the previous two steps is reversed: pumps 106 and 108 are started and then background readings $S1(0)$ and $S2(0)$ are obtained with clean filtered air. Operating system 300 in this way conditions filter areas C1 and C2 before the background readings are made. Operating the pump before taking a background measurement can be particularly advantageous when data is analyzed by comparing a current measurement with the initial measurement, as in certain embodiments described herein.

In certain embodiments, it has been found that conditioning the filter before background measurements is advantageous due to: 1) the compacting of the fibrous material of the filter areas C1 and/or C2 by means of the pressure difference across the tape; and/or 2) allowing the tape to come into equilibrium with gases that pass through the filter, such as water vapor and/or organic compounds, whose presence can change the optical properties of the fibrous material. In one embodiment, the filter (such as filters 321 and 323) are conditioned as follows. First, valve 341 and pumps 106 and 108 are operated such that the flow F is diverted through filter 345. The sample passing through filters 321 and 323 is conditioned, in that the particulates of interest are removed on filter 345. The amount of time required to condition the filters may be pre-determined during testing of the system, and may be several minutes. Thus, after several minutes of operation, for example, filters 321 and 323, have been equilibrated to the ambient concentrations of water vapor and organic compounds, and have also been compacted, allowing areas C1 and C2 to be analyzed in analyzers 112 and 114 to provide background reading S1(0) and S2(0). Next, valve 341 and pumps 106 and 108 are operated such that the flow F is diverted through line 347. The sample passing through filters 321 and 323 thus has any constituents of interest present in the sample, and areas C1 and C2 may be analyzed to in analyzers 112 and 114 to provide measurements S1 and S2. The apparatus and/or method of conditioning are equally applicable to instruments that include only one analyzer.

In one embodiment, filters 321 and 323 are conditioned by removing at least a portion of the constituents of interest from the sample. That is, for example, filter 345, or another device for removing particulates of interest, removes at least a portion of the constituents of interest from flow F. In certain embodiments, it is preferred that a substantial amount of the constituents of interest be removed. Thus, in several embodiments, more that 50%, more than 75%, more than 90%, more than 95%, or more than 99% of the constituents of interest are removed.

In one embodiment, it is advantageous to configure and/or operate system 100 such that the density of the measured constituent of interest on at least two filters (such as filters 321 and 323) accumulates at different rates. Thus, for example, in one embodiment of system 100 combinations of flow rates and filter areas are selected such that the particulate accumulation density on filters (such as filters 321 and 323) occurs at different rates, that is, the rate of accumulation of the mass of particles per time and per unit filter surface area is different for the two filters. It has been found that when this condition is met, it is possible to compensate for the effect of filter loading, as discussed subsequently, which otherwise tends to result in non-linearities in the calculation of particulate concentration in the sample stream. With reference to system 100 or 300, the rate at which the density of particles collected and accumulated from the flow stream increases on the filter is proportional to the concentration of particles in the air sample, the flow rate through the filter, and inversely to the collecting area of the filter.

As one illustration of systems and/or methods having different densities of measured constituent of interest on at least two filters, which is not meant to limit the scope of the present invention, consider measurements on a sample of air having a concentration, B, of optically-absorbing BC particles that may be accumulated on a filter (such as filters 321 and 323). Further consider the air being drawn through a system 300, and specifically through a pair of in-line filters having an area C1, C2, at a volumetric flow rate F1, F2, respectively. The mass of BC flowing through and retained by the filter per unit time is thus the product of B and the corresponding F, and the density of particles passing through the filter per unit time and area is B*F1/C1 and B*F2/C2 for the two filters. Given these definitions, differences in accumulation density on the filters, as provided by certain embodiments, can be achieved in a number of ways including, but not limited to the following:

(a) controlling the air flow through outlets 105 and 107 at different flow rates F1 and F2, while the areas C1 and C2 of filters 321 and 323 are approximately equal.

(b) controlling the air flow through outlets 105 and 107 at approximately identical flow rates F1 and F2, while the areas C1 and C2 of filters 321 and 323 are different.

(c) controlling the air flow through outlets 105 and 107 with additional external switching valves such that the flow streams may be switched on and off in rapid succession, with the result that the total flow passing through the filtration collection area during the analytical period may be varied by controlling the on-off ratio of the switching valves. In this variant, the areas C1 and C2 of through filters 321 and 323 may be either closely similar or substantially different; and the flow rates F1 and F2 (measured when the flow is active) may be either closely similar or substantially different.

These embodiments essentially replicate the operation of two separate analytical instruments by providing two sample accumulation areas operating at different accumulation rates. Such apparatus could operate with one light source and two photo-detectors to measure the accumulation of particulates on two filters.

As a further example, which is not meant to limit the scope of the present invention, the following is an illustrative, simple method of using a differential photometric analyzer. In certain circumstances, the increase of BC on any one filter is sensed by changes in the transmission of light through that filter. One measure of the decreased transmission of light is referred to as attenuation (or "A") according to the following equation: A=100 ln(S0/S), where ln is the natural logarithm, S0 is a background measurement of the intensity of light transmitted through a clean filter, and S is the intensity of light transmitted through the filter when particle-laden. In general the value of S, and thus A, varies with time. In one embodiment, light passes through a portion of the filter that is not within the flow of the sample. This portion remains clear of any particulates and may be used to monitor changes in light intensity. Thus, for every measurement of S, a measurement of S0 is also obtained, and the resulting ratio S0(t)/S(t) accounts for variations in light intensity that might occur over time.

In general, the response of the differential photometric analyzer of system 100 or 300 is linear at low filter loadings (that is, A<<1), and gradually becomes non-linear as A increases. For low filter loadings, system 100 or 300 provides a calibrated response of Bi that approximates the actual value of B. At higher filter loadings, the calibrated response Bi differs from the linear response. Thus, for example, there may be a departure from linearity which, for the purpose of this discussion may be represented, for each analyzer, by:

$$B(\text{non-linear})=B*\{1-k*A\}, \tag{1}$$

where B (non-linear) is the apparatus-dependent nonlinear estimate of the true value of B (that is, the value of B (B1, or B2, below) as measured assuming that the response is linear), and k is the measure of the nonlinearity, or 'compensation parameter' that represents the degree of non-linearity. In the absence of non-linearity, k=0 and the instrument response is uniform: there is no change in instrument response between a fresh filter with zero loading, or a heavily-loaded filter just before the system 300 advances tape 320.

In certain situations with specific combinations of location, season, particle composition and optical properties, the non-linearity effect can be absent and the k value is zero. In other situations, the non-linearity effect can be large and the magnitude of the k value is significantly larger than zero. To improve the performance of any instrument whose measurement principle is based on the determination of an increment, it is clearly advantageous to be able to adapt automatically to all situations, whether they exhibit perfect linearity or serious non-linearity, without requiring any a-priori knowledge of these conditions. A fixed compensation cannot be applied, because one value may be required for one location at one period in time, and another (or zero) value required for a different location, or the same location in a different season.

In one embodiment, consider the combination of measurements from two independently-operating identical instruments. Further, assume that the two measurements give attenuation values of A1 and A2, and that these measurements yield concentration estimates denoted B1 and B2 which are believed to deviate by non-linearity from the "true" value B. These measurements may be combined to give a single improved estimate of B, denoted B0, by combining the two parallel measurements values of Equation 1:

$$B1=B0*\{1-k*A1\}, \text{ and} \qquad \text{Eq. 1a}$$

$$B2=B0*\{1-k*A2\}, \qquad \text{Eq. 1b}$$

It is noted that the attenuation values A1 and A2 are measured directly; and B1 and B2 are the results calculated from A1 and A2, together with other instrumental operational parameters such as the rate of flow of the sample stream through the instrument; the internal area over which the sample is being collected; etc. There are two equations and two unknown quantities of interest: the "true" result B0 which is the data in the absence of any non-linearity; and the non-linearity compensation parameter k.

This pair of equations appears to be linear and amenable to an analytical solution, whose values are determined from one moment to the next. However, the non-linearity effect as represented by the parameter k is not an instantaneous attribute of a single particle, but is intrinsically a collective attribute of the totality of material collected on the filter during its history of operation, and represents the interaction of freshly-arriving material with the entire pre-existing mass of collected material. Consequently, an approach based on the totality of material collected, as opposed to differential instantaneous measurements, is the approach taken here.

Next, define the surface loading density of material of total mass M, collected on the filter spot whose active area is C, as $$D=M/C \qquad \text{Eq. 2}$$

The relationship between the instrumental measurement A and the surface loading density D may be written as:

$$A=A(D), \qquad \text{Eq. 3}$$

which can, for example and without limitation, for the purposes of the following mathematical derivation, be written as:

$$A=(1/k)*\{1-\exp\{-(k*\sigma*D)\}\}, \qquad \text{Eq. 3'}$$

where σ is a fixed instrumental response factor.

The surface loading density D is increasing due to the collection of material from the sampled stream passing through collection area C at flow rate F. The increment in measurement, dA, is related to the increment in surface loading density by the derivative of Equation 3', namely $$dA=\sigma*dD*\exp\{-(k*\sigma*D)\}, \qquad \text{Eq. 4}$$

which shows that for a constant rate of surface loading accumulation dD, the increase in measured signal dA will gradually decrease by an exponential factor based on the product of the total surface loading D, the instrumental response factor σ, and the non-linearity parameter k.

Defining the actual concentration of analyte in the sample stream as B0, then the increment in surface loading density collected during time interval dt is $$dD=\{B0*F/C\}*dt \qquad \text{Eq. 5}$$

Substituting this in Equation 4 yields:

$$dA/dt=\{B0*F*\sigma/C\}*\exp\{-(k*\sigma*D)\}. \qquad \text{Eq. 6}$$

Equation 3' may be rearranged to read:

$$\exp\{-(k*\sigma*D)\}=\{1-k*A\} \qquad \text{Eq. 7}$$

which allows Equation 6 to be written as $$dA/dt=\{B0*F*\sigma/C\}*\{1-k*A\} \qquad \text{Eq. 8}$$

This explicitly exhibits the gradual decrease in instrumental response as a linear function of A.

Taking the natural logarithm of each side of Equation 7:

$$(k*\sigma*D)=-\ln\{1-k*A\} \qquad \text{Eq. 9}$$

The total mass loading density of material on the spot is represented by D. Using Equation 5:

$$D=(F/C)*\int B0(t)dt, \qquad \text{Eq. 10}$$

where the concentration B0 in the sample stream is recognized to be capable of variation with time, and has been integrated for the period starting when the fresh spot of filter tape was advanced into the sample stream.

Next, compare the result of evaluating Equation 9 for data gathered by two parallel measurements, that is, sampling the same concentration B0(t), but having different rates of accumulation of loading D due to being operated with different values of face velocity (F/C). Denote the instruments I1 and I2 by suffixes 1 and 2, and substitute Equation 10 into Equation 9, and including the dependency on time of several of the variables:

$$(k(t)*\sigma*(F1(t)/C1)*\int B0(t)dt)=-\ln\{1-k(t)*A1(t)\}, \text{ and} \qquad \text{Eq. 11a}$$

$$(k(t)*\sigma*(F2(t)/C2)*\int B0(t)dt)=-\ln\{1-k(t)*A2(t)\}. \qquad \text{Eq. 11b}$$

Dividing the last two equations yields:

$$(F1(t)/C1)/(F2(t)/C2)=\ln\{1-k(t)*A1(t)\}/\ln\{1-k(t)*A2(t)\}, \qquad \text{Eq. 12}$$

where $A1(t)=100 \ln(S0(t)/S1(t))$ and $A2(t)=100 \ln(S0(t)/S2(t))$.

Equation 12 is referred to herein as the "Spot Specific Loading Compensation Algorithm" since it relates k to the analytical measurements A1 and A2; and the instrumental operational measurements F1, F2, C1, and C2; in a manner that explicitly requires consideration of the totality of the accumulation of material on the filter spot as represented by the analysis A, rather than a real-time instantaneous measurement as represented by the result B used in Equations 1a and 1b.

With A1 and A2 being determined analytically; and F1, F2, C1, C2 being measured operationally; and with the measurement of F1, F2, C1 and C2 being amenable to improvement in accuracy by a method to be described below; Equation 12 may be solved numerically to deduce a value of k which is the only unknown quantity if the above-mentioned quantities are measured.

Alternatively, the parameter k can be obtained from the equation 3' in other ways: for example using A2/A1 as a function of A1, it is possible to obtain the value of parameter k from the slope of this curve by fitting. Similarly, the fit can be carried out on any of the equations derived from the relationship A=A(D), as described by equation 3.

Having determined k by the above methods, Equations 1a and 1b are used to perform a numerical compensation of the instantaneous data, using the real-time determination of B1 and B2; the analytical measurements A1 and A2; and the value of k which correctly represents the combined effect of the accumulated material on the filter spot.

From these equations the effects of any non-linearity in response of the instrument are eliminated by comparing the data values yielded by two separate instruments operating under analytical conditions that are identical except for the fact that the material loadings are different. In the absence of non-linearity, k=0 and two ideal instruments would give identical data B1 and B2 (equal to the "true" data value B0) at any and all values of A1 and A2. In reality, the comparison of data from two instruments in this manner will always yield the "zero loading" compensated result, together with a value for the non-linearity parameter k that may provide additional information or insight into the nature, composition or properties of the analyte.

In other words, one embodiment of the present method includes the steps of: 1) measuring F1($t$), F2($t$), C1, and C2; 2) measuring A1($t$) and A2(2); 3) solving Eqn. 12 for k(t); 3) Solving Equations 1a and 1b to obtain two estimates of B0 at time t; and 5) Using the estimation of B0 from Equations 1a or 1b having the higher signal-to-noise ratio, or averaging the two estimations of B0 from step 4).

The above example supposes the parallel operation of two identical instruments. Using an apparatus of this or equivalent functionality, it is possible to collect two deposits of particles drawn from the same air stream; and to analyze them simultaneously. The single source of optical illumination 110 creates light that is transmitted through the two filtration areas 132 and 134 and is detected simultaneously by photo-detectors 142 and 144.

Cumulative Nature of "Loading Effect" as Expressed by Parameter K

The mathematical arguments set out above assign a loading compensation parameter k to the aerosol deposit collected on the filter, as a parameterization of the degree to which an increasing accumulated mass of BC material will lead to progressive saturation in the measured optical attenuation A. Experimental evidence shows that this effect can be present or absent at the same location, depending on intrinsically variable or unpredictable aerosol optical, physical or chemical properties. It is therefore reasonable to propose that different types of BC aerosol may intrinsically have different optical loading effects when collected on a filter: for example, fresh emissions of vehicular exhaust collected near to a roadway may have different cumulative optical properties on a filter than well-aged regional aerosols which may have been subjected to accretion and in-atmosphere chemical processing during long-range transport. The loading compensation parameter k is an aggregate property of the totality of the aerosol collected on the filter, and may change with changes in the composition of sampled gases. If, however, filter-based samples are collected at relatively frequent intervals; or, in the case of a tape-based system 100 or 300, if successive spots on the tape are collected and then advanced at frequent intervals; the inventors have found that the value of k as determined from the optical measurements changes and evolve on time-scales that are representative of synoptic changes in air-mass, atmospheric composition, temperature, exposure to sunlight, or other physical properties. This is accomplished by averaging the "instantaneous" value of k (derived from mathematical analysis of the optical data as described in Equations 1 through 12 above) over a retrospective time period which is commensurate with the expected variability period of the aerosol. Although the mathematics suggests that the parameter can be calculated instantaneously, it is known that the "loading saturation effect" is due to the totality of material collected on the filter, not its instantaneous properties. It may therefore be preferred to smooth the derived loading compensation parameter k over longer timescales which may be adjusted according to situation to range from several hours to several days.

Smoothing and Propagation of K

In particular, it is found to be highly advantageous to propagate the averaged value of k across a "tape advance" as shown in FIG. 3 above, in which the analyzed deposit of material on the filter tape is moved forwards when a preset loading limit is reached, and a new analysis is started on a fresh filter tape spot which initially has zero loading. At these values of very light loading of material on the analytical spot, both terms on the right-hand side of Equation 12 are small, leading to the possibility of divergence and amplified bias if any of the measured quantities are perturbed by instrumental noise or other sources of bias. Under these conditions, the previously-determined average value of k continues to be used in the calculation of B0 as offered by Equations 1a and 1b, while the most recent determination of k is combined into a running average with a weighting factor based upon the actual aerosol loadings A1 and A2.

One illustrative but not exclusive example of such an averaging scheme is a weighted autoregressive algorithm. With k(t) denoting the instantaneously-derived value of k at measurement determination time period t; ks(t) as the new smoothed value of k which will be used as a descriptor of the analyte, and kp(t) as the previous smoothed value of k (that, is the value of ks(t'), where t' is the previous time), A1($t$) the attenuation value A1 measured for spot 1 at time period t, as used in Equation 1a above; and Amax as the maximum value of A, at which value when reached, a tape advance is initiated. Denote the degree of smoothing as N, where a value of zero will result in no smoothing, while larger values will result in increasing averaging. For example and without limitation, the weighted autoregressive smoothed compensation parameter is then:

$$ks(t)=\{kp(t)*N+k(t)*(A1(t)/A\max))\}/\{N+(A1(t)/A\max)\} \quad \text{Eq. 13a}$$

In this illustrative example, the value of the smoothing function N may range from zero to any value, and is not required to be an integer.

A second illustrative but not exclusive example of an averaging scheme is given by $$ks(t)=\{kq*(A\max-A1(t))+k(t)*A1(t)\}/A\max \quad \text{Eq. 13b}$$

in which kq is the value of k determined at the end of operation of the previous spot on the filter tape, before the tape advanced to create a new spot; and Amax and A1 have the same meanings as defined above.

The advantage of this invention is that the value of k is carried forwards from the immediate past, and its average is only slowly augmented by the current calculation of k, combined into the previous average with a weighting function proportional to the current value of attenuation A1. In this way, k evolves slowly and the effect of divergent calculations from very lightly-loaded filter spots is reduced. This preserves the stability of k and allows the historical value to be used to calculate very small compensations to B0 at very low values of A when the tape spots are lightly loaded. Since the values of attenuation are small, these compensations are also small: Equations 1a and 1b show that both B1 and B2 are close to B0 when A is small.

However, the determined quantity k is of value in its own right as a descriptor of the analyte, and it is desirable and valuable to maximize the value of this data output by preserving its stability.

Improvement of Accuracy of Face Velocity Used in Calculation

An alternative embodiment improves the accuracy of the Spot Specific Loading Compensation (Equation 12), which depends critically on the relation between the measured attenuations A1 and A2 and the instrumental operational measurements F1, F2, C1 and C2. The quantities (F/C) are the face velocity of the sample air stream from which the particles are collected. Small biases in the measured flow rates F1 and F2; or the assumed instrumental values of the collection areas C1 and C2; could lead to a bias in the calculation of the left-hand terms of Equation 12. Biases in these measurements could have a disproportionate or divergent effect on the calculation of k at low loadings.

At low values of spot loading, the nonlinearity is small and the rate of increase in optical attenuation measured on spot (i) of area Ci through which the air flow is Fi (where (i)=1 or 2) is given by a reduced case of the general form of Equation 6 as $$d/dt\{Ai\}=B0*\sigma*\{Fi/Ci\} \text{ (where } i=1 \text{ or } 2),\qquad \text{Eq. 14}$$

where $\sigma$ is an instrumental constant, B0 is the 'true' value of concentration of the analyte, and the term {F/C} is the face velocity of the air stream through the spot.

The relation between the attenuations measured for the two spots (i)=1, 2 under these specific limiting conditions of low loading will be $$A2/A1=\{F2/C2\}/\{F1/C1\},\qquad \text{Eq. 15}$$

which is a limiting case of Equation 12 for low values of attenuation A1 and A2, before saturation due to loading starts to have an effect. This ratio depends on the exact values of the air flow rates F1 and F2; and also on any mechanical differences in the effective filtration areas C1 and C2. While F1 and F2 are recorded, there is always the possibility of bias in this measurement, or of bias in the effective filtration areas C1 and C2. Since the loading compensation equation 12 depends on small differences between two similar measurements, it is critically important to elucidate all of the parameters involved. Biases in the face velocity (F/C) can result in disproportionate biases in the calculation of B0 and k.

Consequently, values of A1 and A2 are recorded at successive time intervals, and perform a statistical analysis as will be described below. As the attenuations increase, A1 becomes larger more quickly than A2, since it has the larger face velocity. Consequently, the effects of loading saturation start to reduce A1 relative to its expected non-saturation value more quickly than the reduction of A2. The ratio of A2/A1 therefore starts to increase.

Note that in the absence of any non-linearity, the ratio A2/A1 should remain constant, being dictated by the instrumental operational parameters F and C. The value fit by regression and extrapolated to zero loading is the actual in-use value of the face velocity ratio as derived from the optical measurement data itself. Denote this value as AR, defined as $$AR=A2/A1 \text{ as } A1\to 0.\qquad \text{Eq. 16}$$

Measuring these values at well controlled constant values of F1 and F2, denoted as $F1_O$ and $F2_O$, respectively, we now define:

$$FVRF=AR*\{(F1_O)/C1)/(F1_O/C2)\},\qquad \text{Eq. 17}$$

where FVRF, the "Face Velocity Ratio Factor," is an instrument-dependent factor that is derived from the measurements of attenuation data AR and the face velocity ratio {(F1/C1)/(F2/C2)}, which is predicted from the air flow rate measurements and the hardware parameters of spot area C1 and C2, all of which may be subject to slight but significant differences in actual use. FVRF may be applied to the face velocity ratio predicted from nominal technical measurements. This value of the adjustment factor FVRF may be applied to the actual instantaneous values of face velocity, calculated from the flow measurements F1 and F2 which may change slightly from moment to moment during the instrument's operation.

The instrument constants AR and FVRF, also referred to herein as P, are determined from an analysis of a sample in a system in the linear response range of low filter loadings. As discussed subsequently, instrument constant P can be used to correct for system non-linearities in the measurement of the concentration of the constituents of interest. In certain embodiments, P is determined in the system, such as system 100 or 300, either once or between certain measurements. In certain other embodiments, P is determined for the system by using another system which is used for determining such constants. Thus, for example, the constant can be applied to more than one system 100 or 300.

The relation between the instrumental attenuation ratio AR and the measured flow values F1 and F2 may thus, in one embodiment, form the basis for the instrument dependent parameter FVRF that incorporates a number of measured parameters such as, but not limited to, small biases in the assumed values of the collecting spot areas C1 and C2, and other mechanical factors. This Ratio Factor will be preserved even if the flow rates F1 and F2 change slightly. We can, in certain embodiments, use this constant Ratio Factor; together with the measured instrumental parameters F1, F2, C1 and C2, to adjust the value of face velocity (F/C) which is used in Equation 8 to calculate B0 from the measurements of A (and its rate of change, dA/dt), and the smoothed value of k which is changing only slowly.

The ratio AR, expressed in the form of FVRF combined with the measured parameters F1 and F2 and the instrumental parameters C1 and C2, is used as the optimal value of the term on the left-hand side of Equation 12, the Spot Specific Loading Compensation Algorithm. This ratio as determined by the procedure described above is used in Equation 12 which is re-written as $$FVRF*\{(F2(t)/C2)/(F1(t)/C1)\}=\ln(1-k(t)*A2(t))/\ln(1-k(t)*A1(t)),\qquad \text{Eq. 18}$$

to be solved numerically to yield an accurate determination of the loading compensation parameter k(t). This method of performing a fit to data acquired under optimal operating conditions, while avoiding the possibly disproportionate influence of data calculated under unstable conditions, provides an improved determination of the quantities B0 and k which describe the sample.

Alternatively, Equations 17 and 18 may be combined to yield:

$$AR*\{F2(t)/F2_O\}/\{F1(t)/F1_O\}=\ln(1-k(t)*A2(t))/\ln(1-k(t)*A1(t)),\qquad \text{Eq. 19}$$

which shows that measurements of the spot sizes C1, C2, are not required to determine k(t).

In this manner, the aerosol descriptor derived from an interpretation of k may be smoothed and averaged over periods of time that are commensurate with the time-scales of its expected variation, while the calculations based upon data with very small values of both denominator and numerator have less opportunity to disproportionately perturb the average. Any effects of minor biases in the determination of face velocity, upon which the calculations are based by the determination of small differences in both numerator and denominator, are reduced by performing an extrapolation and statistical fit to the evolution of the data. It is a claim of this invention that the calculation and smoothing of the value of k in a manner similar to that described, yields a result that is more mathematically stable and consequently is of greater utility as a descriptor of the properties of the analyte.

An alternative one embodiment of the present method includes the steps of: 1) determining AR for the instrument from pre-measurement determinations of A1 and A2 at accurately measured values of $F1_0$ and $F2_0$ and using Eqn. 16; 2) measuring F1(t), F2(t), C1, and C2; 3) determining FVRF from AR, F1(t), F2(t), C1, and C2 using Eqn. 17; 4) solving Eqn. 18 for k(t); 5) solving Equations 1a and 1b to obtain two estimates of B0 using k(t); and 6) using the estimation of B0 from Equations 1a or 1b having the higher signal-to-noise ratio, or averaging the two estimations of B0 from step 4).

As described herein, there are several alternative embodiment of the method described in the previous paragraph, which may be used individually or in combination.

In one alternative embodiment, the value of k(t) solved for in step 4) is used to calculate a new value of k (specifically ks(t) from Equation 13a or 13b), which is then used in place of k(t) in steps 5) and 6). In other words, the values of k(t) determined at each time are stored and used to produce a time-smoothed value ks(t) which is used to determine the concentration of the constituents of interest.

In another alternative embodiment, C1 and C2 are not required to determine k(t) in steps 2-4, above. Specifically, step 2) may be modified to only require measuring F1(t) and F2(t), and step 3) may be modified to solving Eqn. 19 for k(t).

In yet another alternative embodiment, the filters are pre-conditioned to the prevailing concentrations of water vapor moisture and/or organic compounds in the sample before being analyzed in step 2). In this embodiment, valve 342 is operated, as discussed above, to first send the flow F through filter 345 to provide flow filtered of constituents of interest to analyzers 112 and 114, and then, after several minutes, valve 342 is operated to allow the unfiltered sample to flow through the analyzers and to thus measure the concentration of the constituents of interest as they vary with time.

Embodiments have been described using the example of the optical analysis of suspended particles for 'Black Carbon' content as performed by a differential photometric analyzer. It will be understood by those in the art that this method is applicable to a wide range of analytical instruments whose analysis is based on determining the rate of change of an accumulation.

We claim:
1. An apparatus to measure constituents of interest in a sample having a concentration, B, said apparatus comprising:
a first analyzer including a first filter portion having a first area, C1, operable to accumulate constituents of interest in a first portion of the sample having a first flow rate, F1, and a detector operable to measure a first attenuation of light through the accumulated constituents of interest on said first filter portion as a function of time, A1, of the constituent of interest on said first filter portion;
a second analyzer including a second filter portion having a second area, C2, operable to accumulate constituents of interest in a second portion of the sample having a second flow rate, F2, and a detector operable to measure a second attenuation of light through the accumulated constituents of interest on said second filter portion as a function of time, A2, of the constituent of interest on said second filter portion; and
a processing device having a processor operable to receive the first detector and second detector measurements and provide an indication of the constituents of interest in the flow, where the processor is programmed to determine an estimate of the concentration of the constituents of interest by:
receiving an instrument calibration, P, where P is determined for the apparatus in the limit of A1→0,
determining current values of F1 and F2,
determining current values of A1 and A2,
determining, using A1, a first measure of a concentration estimate of the constituents of interest from said first filter portion, B1,
determining, using A2, a second measure of a concentration estimate of the constituents of interest from said second filter portion, B2,
calculating the current value of the concentration B of the constituents of interest in the sample using P, current values of F1, A1, B1, F2, A2, B2, and B.

2. The apparatus of claim 1, wherein calculating for the concentration B of the constituents of interest in the sample includes estimating a compensation to the measurements of one or more of B1 or B2, and applying said compensation to the measurements to obtain an estimate of B.

3. The apparatus of claim 2, wherein said estimating a compensation to the measurements of one or more of B1 or B2 includes estimating a compensation based on current measurements of F1, A1, B1, F2, A2, and B2.

4. The apparatus of claim 2, wherein said estimating a compensation to the measurements of one or more of B1 or B2 includes estimating a compensation based on previous measurements of F1, A1, B1, F2, A2, and B2.

5. The apparatus of claim 1, where P is AR, where AR=A2/A1 as determined for the apparatus under conditions where F1=$F1_0$ and F2=$F2_0$ and in the limit of A1→0, and wherein said calculating includes:
determining k that satisfies $$AR*\{F2/F2_0\}/\{F1/F1_0\}=\ln(1-k*A2)/\ln(1-k*A1); \text{ and}$$

estimating B using the values of B1, B2, A1, A2, and k.

6. The apparatus of claim 1, where P is FVRF, where FVRF=AR*{(F1$_0$/C1)/(F2$_0$/C2)}, where AR=A2/A1 as determined for the apparatus under conditions where F1=$F1_0$ and F2=$F2_0$ and in the limit of A1→0, and wherein said calculating includes:
determining k that satisfies $$FVRF*\{(F2/C2)/(F1/C1)\}=\ln(1-k*A2)/\ln(1-k*A1);$$
$$\text{and}$$

estimating B using the values of B1, B2, A1, A2, and k.

7. The apparatus of claim 1, wherein said first attenuation and said second attenuation result from absorption of light at two or more wavelengths through said first filter portion and said second filter portion, respectively.

8. The apparatus of claim 1, wherein the ratio (F1/C1) is different than the ratio (F2/C2).

9. The apparatus of claim 1, where said constituents of interest include carbon black.

10. The apparatus of claim 1, wherein said first analyzer and said second analyzer is a differential photometric analyzer.

11. The apparatus of claim 1, wherein said first filter portion and said second filter portion are portions of one or more filter tapes, and where the processing device is further programmed to execute the steps of advancing more of said one or more filter tapes to a fresh filter when the estimated concentration is equal to or greater than a predetermined value.

12. The apparatus of claim 1, wherein said first filter portion and said second filter portion are portions of one or more filter tapes, and where the processing device is further programmed to execute the steps of advancing more of said one or more filter tapes to a fresh filter when the estimated concentration is equal to or greater than a predetermined value, and wherein said previous measurements of F1, A1, B1, F2, A2, and B2 are obtained before the filter is advanced.

13. A method for measuring constituents of interest in a sample having a concentration, B, performed in an apparatus including a first analyzer including a first filter portion having a first area, C1, and a first detector; and a second analyzer including a second filter portion having a second area, C2, and a second detector, the method including:
   accumulating constituents of interest on the first filter portion from a first portion of the sample having a first flow rate, F1, at the first analyzer;
   measuring a first attenuation of light through the accumulated constituent of interest on the first filter portion as a function of time, A1;
   determining, using A1, a first measure of a concentration estimate of the constituents of interest from said first filter portion, B1;
   accumulating constituents of interest on the second filter portion from a second portion of the sample having a second flow rate, F2, at the second analyzer;
   measuring a second attenuation of light through the accumulated constituent of interest on the second filter as a function of time, A2;
   determining, using A2, a second measure of a concentration estimate of the constituents of interest from said second filter portion, B2;
   receiving an instrument calibration, P, where P is determined for the apparatus in the limit of A1→0,
   determining current values of F1 and F2;
   determining current values of A1 and A2; and
   calculating the current value of the concentration B of the constituents of interest in the sample using P, and current values of F1, A1, B1, F2, A2, B2, and B.

14. A computer program product, comprising a non-transitory computer usable medium having computer readable program code embodied therein, said computer readable program code adapted to be executed to implement a method for measuring constituents of interest in a sample having a concentration, B, performed in an apparatus including a first analyzer including a first filter portion having a first area, C1, and a first detector; and a second analyzer including a second filter portion having a second area, C2, and a second detector, the method including:
   accumulating constituents of interest on the first filter portion from a first portion of the sample having a first flow rate, F1, at the first analyzer;
   measuring a first attenuation of light through the accumulated constituent of interest on the first filter portion as a function of time, A1;
   determining, using A1, a first measure of a concentration estimate of the constituents of interest from said first filter portion, B1;
   accumulating constituents of interest on the second filter portion from a second portion of the sample having a second flow rate, F2, at the second analyzer;
   measuring a second attenuation of light through the accumulated constituent of interest on the second filter as a function of time, A2;
   determining, using A2, a second measure of a concentration estimate of the constituents of interest from said second filter portion, B2;
   receiving an instrument calibration, P, where P is determined for the apparatus in the limit of A1→0,
   determining current values of F1 and F2;
   determining current values of A1 and A2; and
   calculating the current value of the concentration B of the constituents of interest in the sample using P, and current values of F1, A1, B1, F2, A2, B2, and B.

* * * * *